United States Patent [19]

Helal

[11] Patent Number: 4,578,080
[45] Date of Patent: Mar. 25, 1986

[54] JOINT PROSTHESES

[76] Inventor: Basil H. Helal, Broomer Cottage, Churchgate, Cheshunt, Hertfordshire, England

[21] Appl. No.: 530,302

[22] Filed: Sep. 8, 1983

[51] Int. Cl.⁴ ............................................... A61F 1/00
[52] U.S. Cl. .................................... 623/13; 128/92 C; 128/335.5; 128/334 R
[58] Field of Search ................. 128/92 C, 92 B, 335.5, 128/334 R; 3/1, 1.9, 1.91

[56] References Cited

U.S. PATENT DOCUMENTS

| | | |
|---|---|---|
| 3,462,765 | 8/1969 | Swanson . |
| 3,545,008 | 12/1970 | Bader, Jr. ..................................... 3/1 |
| 3,577,837 | 5/1971 | Bader, Jr. ..................................... 3/1.9 |
| 3,739,403 | 6/1973 | Nicole . |
| 3,745,590 | 7/1973 | Stubstad ..................................... 3/1.9 |
| 3,818,513 | 6/1974 | Pillet . |
| 4,158,893 | 6/1979 | Swanson . |
| 4,204,284 | 5/1980 | Koeneman . |
| 4,246,662 | 1/1981 | Pastrick . |
| 4,313,232 | 2/1982 | Habal . |
| 4,367,562 | 1/1983 | Gauthier . |

Primary Examiner—Richard J. Apley
Assistant Examiner—David J. Isabella
Attorney, Agent, or Firm—Hall, Myers & Rose

[57] ABSTRACT

A finger knuckle joint prosthesis includes an elastomeric main body comprised of a central hinging part and two intramedullary stems. Extending from the main body towards the thumb is an integral strip. An integral tendon-retaining flap extends from the opposite side of the body, and a channel extends along between the strip and the flap for receiving one-third of a slit leader of a finger, the other two-thirds of which press the flap face-to-face against the strip.

8 Claims, 2 Drawing Figures

JOINT PROSTHESES

BACKGROUND OF THE INVENTION

1. Field of the Invention

This invention relates to joint prostheses, particularly to finger knuckle joint prostheses.

2. Description of the Prior Art

U.S. Pat. No. 4,367,562 discloses an implantable joint prosthesis, to restore a finger joint or toe joint and consisting of a one-piece body of a material which is flexible and elastic and has tapering intramedullary stems extending in opposite directions from a central portion. The central portion is formed at an intermediate location with a relatively thin region defining the articulation axis and includes a pair of bulges which project in all directions transverse to the axis of the body outwardly of the respective stems on either side of this region and between the articulation region and the respective stem. The rounded bulge at the proximal side of the prosthesis is larger in volume than the rounded bulge at the distal side.

U.S. Pat. No. 3,745,590 discloses a prosthesis for use at joints, in particular those which require unrestricted orbiting motion such as the base of the thumb, carpal bones of the wrist and shoulder joints. The prosthesis comprises a molded body portion which replaces at least the articulating portion of the bone to be treated, and one or more ligamentous elements. The body portion is made of a biocompatible elastomer, especially one which is reinforced with a fibrous material such as a web or mesh of Dacron or Teflon. The ligamentous element can be a cord, a flat tape or a tube such as a fabric tube of Dacron or Teflon, and in some embodiments is protected against tissue ingrowth over at least its intermediate length. In a carpal-metacarpal prosthesis for a thumb, for example, the body portion also has a metacarpal stem portion having a tissue-ingrowth-receiving surface, such as a complete or partial covering of Dacron velour, the core of such stem being a biocompatible elastomer. The ligamentous element is tied or otherwise attached to a body tissue, for example to a bone or a tendon, in order to hold the articulating end of the body portion in its natural position. In an example in which the prosthesis is a carpal-metacarpal thumb prosthesis, the body portion is inserted in the metacarpal bone, the trapezium is excised and two ligamentous elements are brought to the flexor carpi radialis where their outer ends are inserted through an incision in the distal end zone of that tendon and tied thereto with slight slackness.

SUMMARY OF THE INVENTION

According to one aspect of the present invention there is provided a finger knuckle joint prosthesis comprising a main part for insertion between the two bones of the joint, first and second intermedullary stems extending from respective opposite ends of said main part, a tendon-retaining part mounted on the main part and arranged to retain a tendon, and surface portions of the main part and the tendon-retaining part defining a channel for receiving a portion of the tendon in a desired position over the main part.

This prosthesis has the advantage that the surface portions of the channel retain the tendon against falling from the knuckle in the case which the finger has drifted away from the thumb.

According to another aspect of the present invention, there is provided a joint prosthesis comprising a main body which is comprised of a relatively flexible material and which is made relatively thin at a zone thereof in order that bending of said body may occur primarily at said zone during use, and first and second reinforcing members extending from said zone away from each other and comprised of a relatively stiff material in order to ensure that bending of said body occurs primarily at said zone.

BRIEF DESCRIPTION OF THE DRAWINGS

In order that the invention may be clearly understood and readily carried into effect, reference will now be made, by way of example, to the accompanying drawings, in which.

DESCRIPTION OF THE PREFERRED EMBODIMENT

Figure 1:
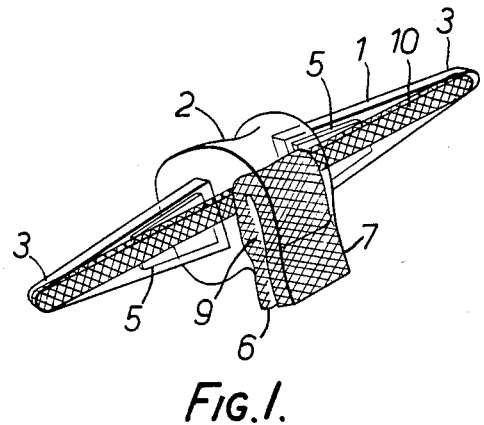
FIG. 1 is a perspective view of a finger knuckle joint prosthesis with a tendon-retaining flap thereof closed.
Figure 2:
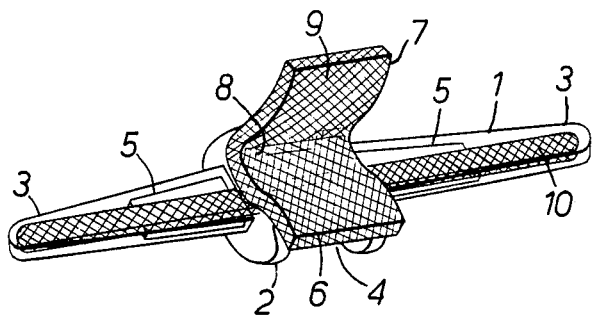
FIG. 2 is another perspective view of the prosthesis with the flap open.

Referring to the drawings, the prosthesis shown comprises a main body 1 of a relatively flexible material, in this case silicone elastomer. This body 1 comprises a central hinging part 2 and two stems 3 extending respectively distally and proximally from the part 2. The part 2 is formed transversely with a U-shaped channel 4, so that centrally the part 2 is relatively thin in order that, in use, bending of the body 1 may naturally occur there. However, since the body 1 is relatively flexible, bending may also occur near where the stems 3 join the part 2. Therefore, two reinforcing members 5 of a relatively stiff material, in this case polypropylene, have been moulded into the body 1 so as to extend respectively distally and proximally from the intended bending zone of the body 1. Extending from the body 1 in the direction of the thumb and formed integrally with the body 1 is a strip 6. The tendon-retaining flap 7 extends from that side of the body 1 furthest from the thumb, where it is integral with the body 1, towards the thumb and can lie face-to-face on the strip 6. Between the strip 6 and the fixation of the flap 7 and extending along the prosthesis is a shallow channel 8. Extending within the strip 6, the part 2 and the flap 7 so as to reinforce the strip 6 and the flap 7 is a strip 9 of a relatively flexible material, in this case dacron ribbon. Another reinforcing strip 10 of relatively flexible material, again dacron ribbon, extends within the two stems 3 and the part 2.

In case of severe rheumatism of the hands, the fingers drift away from the thumb and the leaders or tendons on the backs of the fingers tend to fall off the knuckles in a sense away from the thumb. During insertion of the prosthesis shown, the leader of the knuckle joint being replaced is slit longitudinally to divide it into two leader sections, one being one-third of its width and the other being two-thirds of its width. the one-third width section is laid in the channel 8, the flap 7 is closed, and the two-thirds section laid upon the outside of the flap 7. The two-thirds section holds the flap 7 closed, the strip 6 supporting the flap 7. The slit along the leader is long enough to allow the leader to perform its full normal excursion at the knuckle joint.

I claim:

1. A joint prosthesis, comprising: an elongated body of resilient biocompatible material having an enlarged main part for positioning between two bones of a joint, first and second intermedullary stems projecting from respective opposite points of said main part, tendon retaining means for retaining at least a portion of a tendon, said tendon-retaining means comprises a flap integrally connected to said main part and adapted to lie thereover defining a continuous channel therebetween for receiving and slidably guiding at least part of the tendon, where the tendon is positionally stabilized relative to said main part and is contiguous with said main part.

2. A prosthesis according to claim 1 where said flap is held against said main part by an elongated portion of the tendon and the remaining portion of the tendon is located in the channel.

3. A prosthesis according to claim 1 where said tendon retaining means further comprises a strip member attached to and projecting from said main part which is capable of coacting with said flap.

4. A prosthesis according to claim 3 further comprising a relatively flexible reinforcing core element incorporated in said strip member.

5. A prosthesis according to claim 1 further comprising a relatively flexible reinforcing core element incorporated in said tendon-retaining means.

6. A finger joint prosthesis, comprising:
(a) an elongated body of resilient biocompatible material having a main part for positioning between two bones of the joint, first and second intermedullary stems projecting from respective opposite points of said main part,
(b) tendon-retaining means for positionally stabilizing a tendon, said tendon retaining means being formed integrally with said main part, said tendon retaining means comprising an elongated flap member wherein said flap member is contiguous with an outer surface of said main part and separated therefrom by a continuous channel such that at least a portion of the tendon is secured in said channel between said flap member and said main part, to stabilize the positon of said tendon relative to said body.

7. A prosthesis according to claim 6 where said main part includes a strip member which cooperates with said flap member to secure at least a portion of said tendon.

8. A prosthesis according to claim 6 where said tendon-retaining means incorporates a relatively flexible reinforcing core element.

* * * * *